United States Patent [19]
Scheel-Krüger et al.

[11] Patent Number: 5,998,405
[45] Date of Patent: Dec. 7, 1999

[54] FUSED TROPANE-DERIVATIVES AS NEUROTRANSMITTER REUPTAKE INHIBITORS

[75] Inventors: Jørgen Scheel-Krüger, Glostrup; Gunnar M. Olsen, Copenhagen N.; Elsbet Østergaard Nielsen, Copenhagen K; Bjarne Hugo Dahl, Allerød; Leif Helth Jensen, Copenhagen V, all of Denmark

[73] Assignee: NeuroSearch A/S, Ballerup, Denmark

[21] Appl. No.: 09/051,107

[22] PCT Filed: Nov. 4, 1996

[86] PCT No.: PCT/EP96/04793

§ 371 Date: Jun. 4, 1998

§ 102(e) Date: Jun. 4, 1998

[87] PCT Pub. No.: WO97/16451

PCT Pub. Date: May 9, 1997

[30] Foreign Application Priority Data

Feb. 13, 1996 [DK] Denmark .................................. 0146/96
Nov. 2, 1996 [DK] Denmark .................................. 1223/95

[51] Int. Cl.[6] .......................... A61K 31/46; A61K 31/55; C07D 471/18
[52] U.S. Cl. ............................. 514/214; 546/79; 546/98; 546/99; 540/479; 540/586; 514/290; 514/296
[58] Field of Search .................................. 546/79, 98, 99; 540/479, 586; 514/214, 290, 296

[56] References Cited

PUBLICATIONS

Yousef et al., "A Preliminary Report: A New Scale to Identify the Pseudodementia Syndrome," International Journal of Geriatric Psychiatry, vol. 13, pp. 389–399, 1998.
Wood et al., "Pharmacotherapy of obsessive compulsive disorder—experience with fluoxetine," International Clinical Psychopharmacology, vol. 8, No. 4, pp. 301–306, 1993.
den Boer, "Psychopharmacology of Comorbid Obsessive–Compulsive Disorder and Depression," J. Clin. Psychiatry, vol. 58, Suppl. 8, pp. 17–19, 1997.
Kaye et al., "Serotonin Neuronal Function and Selective Serotonin Reuptake Inhibitor Treatment in Anorexia and Bulimia Nervosa," Biol. Psychiatry, vol. 44, pp. 825–838, 1998.
Mayer et al., "The Use of Selective Serotonin Reuptake Inhibitors in Eating Disorders," J. Clin. Psychiatry, vol. 59, Suppl. 15, pp. 28–34, 1998.
Miura et al., "Improving Effects of FG–7080, a Serotonin Reuptake Inhibitor, on Scopolamine–Induced Performance Deficits of Memory Tasks in Rats," Japan J. Pharmacol., vol. 62, pp. 203–206, 1993.
Altman et al., "Role of serotonin in memory: Facilitation by alaproclate and zimeldine," Psychopharmacology, vol. 84, pp. 496–502, 1984.
Meneses et al., "Effect of Fluoxetine on Learning and Memory Involves Multiple 5–HT Systems," Pharm. Biochem. and Behavior, vol. 52, No. 2, pp. 341–346, 1995.

Tyrer et al., "5–HT drugs in anxiety," J. Psychopharmacology, vol. 7, No. 1, pp. 96–97, 1993.

(List continued on next page.)

*Primary Examiner*—Mukund J. Shah
*Assistant Examiner*—Ann M. Kessinger
*Attorney, Agent, or Firm*—Birch, Stewart, Kolasch & Birch, LLP

[57] ABSTRACT

The present invention discloses compounds of the formula,

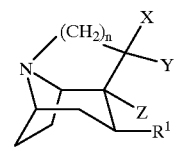

or any of its enantiomers or any mixture thereof, a pharmaceutically acceptable addition salt thereof or the N-oxide thereof wherein X and Y together forms $=O$, $=S$, $=NOR^2$, $=CR^3R^4$, $=N-CN$, $=N-NR^7R^8$, $-(CH_2)_m-$, or $-W'-(CH_2)_p-W''-$, or one of X and Y is hydrogen and the other is $-OR^5$, $-SR^5$, or $-NR^5R^6$ Z is hydrogen, $-COOR^9$;

$R^3$ and $R^4$ are independently hydrogen, halogen, alkyl, cycloalkyl, cycloalkylalkyl, alkenyl, alkynyl, alkoxy, aryl, arylalkyl, or $-(CH_2)_q-COOR^2$;

$R^2$, $R^5$ and $R^6$ are independently hydrogen, alkyl, cycloalkyl, cycloalkylalkyl, alkenyl, alkynyl, aryl, or arylalkyl, $-CO$-alkyl, or $-SO_2$-alkyl;

$R^7$ and $R^8$ are independently hydrogen, alkyl, cycloalkyl, cycloalkylalkyl, alkenyl, alkynyl, aryl, or arylalkyl;

$R^9$ is alkyl, alkenyl or alkynyl;

$R^1$ is alkyl, alkenyl, alkynyl, aryl, or arylalkyl;

where said aryl groups may be substituted one or more times with substituents selected from the group consisting of halogen, $CF_3$, CN, alkoxy, cycloalkoxy, alkyl, cycloalkyl, alkenyl, alkynyl, amino and nitro;

W' and W'' are each independently O or S;

n is 1, 2, 3, or 4;

m is 2, 3, 4, or 5;

p is 1, 2, 3, 4, or 5; and q is 0, 1, 2, 3,or 4.

The compounds possess valuable properties as monoamine neurotransmitter, i.e dopamine, and serotonine, reuptake inhibitors.

8 Claims, No Drawings

OTHER PUBLICATIONS

Fava et al., "Anger Attacks in Depressed Outpatients and Their Response of Flouxetine," Psychopharmacology Bulletin, vol. 27, No. 3, pp. 275–279, 1991.

Liebowitz, "Depression With Anxiety and Atypical Depression," J. Clin. Psychiatry, vol. 54, Suppl. 2, pp. 10–14, 1993.

Nutt, "Management of Patients With Depression Associated With Anxiety Symptoms," J. Clin. Psychiatry, vol. 58, Suppl. 8, pp. 11–16, 1997.

Birmaher et al., "Pharmacologic Treatment for Children and Adolescent with Anxiety Disorders," Child and Adolescent Psychopharmacology, Bol. 45, No. 5, pp. 1187–1204, Oct. 1998.

Kasper et al., "Safety and Antidepressant Efficacy of Selective Serotonin Re–uptake Inhibitors," Human Psychopharmacology, vol. 9, pp. 1–12, 1994.

Morrison et al., "Organic Chemistry," Allyn & Bacon, 3rd Edition, pp. 457,518,519,630,632,633 and 715, 1981.

March, "Advanced Organic Chemistry: Reactions, Mechnisms and Structure," McGraw–Hill, p. 814, 1997.

FUSED TROPANE-DERIVATIVES AS NEUROTRANSMITTER REUPTAKE INHIBITORS

This application is the national phase under 35 U.S.C. §371 of prior PCT International Application No., PCT/EP96/04793, which has an International filing date of Nov. 4, 1996, which designated the United States of America, the entire contents of which are hereby incorporated by reference.

The present invention relates to novel fused tropane-derivatives which are monoamine neurotransmitter, i.e dopamine, serotonin and noradrenaline, re-uptake inhibitors. In particular, the present invention relates to novel fused tropane-derivatives which are potent serotonin re-uptake inhibitors and therefore useful in the treatment of disorders or diseases responsive to the inhibition of serotonin re-uptake, such as depression and related disorders, obsessive compulsive disorders, panic disorders, memory deficits, attention deficit hyperactivity disorder, obesity, anxiety and eating disorders.

BACKGROUND OF THE INVENTION

The brain consists of a plurality of neurons that communicate with each other via chemical messengers. Each neuron generates neurochemicals, referred to as neurotransmitters; and the neurotransmitters act at sites on the cellular membrane of neurons, the sites being referred to as receptors. One group of neurotransmitters, referred to as the monoamine neurotransmitters, includes serotonin, dopamine and noradrenaline.

Monoamine neurotransmitters are released into the synaptic cleft in order to stimulate postsynaptic receptor activity. The removal (or inactivation) of monoamine neurotransmitters occurs mainly by a reuptake mechanism into presynaptic terminals. By inhibiting the re-uptake an enhancement of the physiological activity of monoamine neurotransmitters occur.

Noradrenalin and serotonin re-uptake inhibitors are currently used as pharmaceuticals in anti-depressant therapy (Desipramine, Nortriptyline, and Protriptyline are inhibitors of noradrenaline-reuptake and Imipramine and Amitriptyline are mixed serotonine-reuptake and noradrenaline-reuptake inhibitors).

The pathophysiology of major affective illness is poorly understood, and several neurotransmitters have been implicated in the pathophysiology of major depression. However, several lines of preclinical and clinical evidence indicate that an enhancement of serotonin-mediated neurotransmission might underlie the therapeutic effect of the most recent and currently used drugs in anti-depressant therapy: Fluoxetine, Citalopram and Paroxetine.

Paradoxical serotonin re-uptake inhibitors inhibit the serotonin transporter within minutes whereas their full anti-depressant effect is seen only after three to four weeks of treatment, indicating that re-uptake inhibition per se is not responsible for the antidepressant response, but rather that further adaptive changes underlie and/or contribute to their therapeutic effect. The delayed onset of anti-depressant effect is considered to be a serious drawback to currently used monoamine re-uptake inhibitors.

The compounds provided with the present invention are potent serotonin (5-hydroxy-tryptamine, 5-HT) re-uptake inhibitors. The compounds of the invention also have noradrenaline and dopamine re-uptake inhibiting activity, the serotonin re-uptake and the noradrenaline re-uptake inhibiting activity of the compounds of the invention being stronger than the dopamine re-uptake inhibiting activity of the compounds, see table below.

A strong dopamine re-uptake inhibiting activity is currently considered with the risk of undesirable central stimulating effects. On the other hand, an activating effect on the mesolimbic dopamine system is currently believed to underlay the commen mechanism of current antidepressant treatment by a mechanism which enhances the endogenous reward system. Compounds with a strong serotonin re-uptake inhibiting activity combined with a well balanced moderate dopamine re-uptake inhibiting activity may therefore provide agents with a rapid onset of anti-depressant effect.

The serotonergic neural system of the brain have been shown to influence a variety of physiologic functions, and the compounds of the present invention are predicted to have the ability to treat in mammals, including humans, a variety of disorders associated with this neural system, such as eating disorders, depression, obsessive compulsive disorders, panic disorders, alcoholism, pain, memory deficits and anxiety. Therefore, the present invention also provides methods of treating several disorders linked to decreased neurotransmission of serotonin in mammals. Included among these disorders are depression and related disorders such as pseudodementia or Ganser's syndrome, migraine pain, bulimia, obesity, pre-menstrual syndrome or late luteal phase syndrome, alcoholism, tobacco abuse, panic disorder, anxiety, post-traumatic syndrome, memory loss, dementia of ageing, social phobia, attention deficit hyperactivity disorder, chronic fatigue syndrome, premature ejaculation, erectile difficulty, anorexia nervosa, disorders of sleep, autism, mutism or trichotillomania.

In addition, compounds with dopamine re-uptake inhibiting activity are also considered useful for the treatment of Parkinsonism, depression, obesity, narcolepsy, drug addiction or misuse, attention-deficit hyperactivity disorders and senile dementia. Dopamine re-uptake inhibitors enhances indirectly via the dopamine neurones the release of acetylcholin and are therefore useful for the treatment of memory deficits, e.g. in Alzheimers disease and presenile dementia, and chronic fatigue syndrome. Noradrenaline re-uptake inhibitors are considered useful for enhancing attention, alertness, arousal, vigilance and for treating depression.

OBJECTS OF THE INVENTION

It is an object of the present invention to provide novel fused tropane-derivatives which are monoamine neurotransmitter re-uptake inhibitors. In particular it is an object of the present invention to provide potent serotonin re-uptake inhibitors which are useful for the treatment of depression and related diseases, obsessive compulsive disorders, panic disorders, memory deficits, attention deficit hyperactivity disorder, obesity, anxiety and eating disorders.

Another object of the present invention is to provide novel pharmaceutical compositions containing the novel fused tropane-derivatives which are useful for the treatment of disorders or diseases responsive to the monoamine neurotransmitter re-uptake inhibiting activity of the compounds of the invention.

Still another object of the invention is to provide a method of treating diseases or disorders responsive to the inhibition of monoamine neurotransmitter re-uptake and in particular serotonin re-uptake, such as depression and related diseases obsessive compulsive disorders, panic disorders, memory deficits, attention deficit hyperactivity disorder, obesity, anxiety and eating disorders.

Other objects will become apparent hereinafter to one skilled in the art.

THE PRESENT INVENTION

The invention then, inter alia, comprises the following, alone or in combination:

A compound having the formula,

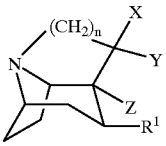

or any of its enantiomers or any mixture thereof, a pharmaceutically acceptable addition salt thereof or the N-oxide thereof
wherein X and Y together forms $=O$, $=S$, $=NOR^2$, $=CR^3R^4$, $=N-CN$, $=N-NR^7R^8$, $-(CH_2)_m-$, or $-W'-(CH_2)_p-W''-$, or one of X and Y is hydrogen and the other is $-OR^5$, $-SR^5$, or $-NR^5R^6$ Z is hydrogen, $-COOR^9$;

$R^3$ and $R^4$ are independently hydrogen, halogen, alkyl, cycloalkyl, cycloalkylalkyl, alkenyl, alkynyl, alkoxy, aryl, arylalkyl, or $-(CH_2)_q-COOR^2$;

$R^2$, $R^5$ and $R^6$ are independently hydrogen, alkyl, cycloalkyl, cycloalkylalkyl, alkenyl, alkynyl, aryl, or arylalkyl, $-CO$-alkyl, or $-SO_2$-alkyl;

$R^7$ and $R^8$ are independently hydrogen, alkyl, cycloalkyl, cycloalkylalkyl, alkenyl, alkynyl, aryl, or arylalkyl;

$R^9$ is alkyl, alkenyl or alkynyl;

$R^1$ is alkyl, alkenyl, alkynyl, aryl, or arylalkyl;

where said aryl groups may be substituted one or more times with substituents selected from the group consisting of halogen, $CF_3$, CN, alkoxy, cycloalkoxy, alkyl, cycloalkyl, alkenyl, alkynyl, amino and nitro;

W' and W" are each independently O or S;

n is 1, 2, 3, or 4;

m is 2, 3, 4, or 5;

p is 1, 2, 3, 4, or 5; and q is 0, 1, 2, 3, or 4;

a compound as above which is (1S,2S,4S,7R)-2-(3,4-Dichlorophenyl)-8-azatricyclo[5.4.0.0$^{4,8}$]undecan-11-one, (1S,2S,4S,7R)-2-(3,4-Dichlorophenyl)-8-azatricyclo[5.4.0.0$^{4,8}$]undecan-11-ol, (1S,3S,4S,8R)-3-(3,4-Dichlorophenyl)-7-azatricyclo[5.3.0.0$^{4,8}$]decan-5-one, (1S,3S,4S,8R)-3-(3,4-Dichlorophenyl)-7-azatricyclo[5.3.0.0$^{4,8}$]decan-5-one O-methyl-oxime, (1S,2S,4S,7R)-2-(4-Chlorophenyl)-8-azatricyclo[5.4.0.0$^{4,8}$]undecan-11-one, (1S,3S,4S,8R)-3-(3,4-Dichlorophenyl)-7-aza-tricyclo[5.3.0.0$^{4,8}$]decan-5-ol, (1S,3S,4S,8R)-3-(3,4-Dichlorophenyl)-7-azatricyclo[5.3.0.0$^{4,8}$]dec-5-yl acetate, (1S,3S,4S,8R)-3-(3,4-Dichlorophenyl)-7-azatricyclo[5.3.0.0$^{4,8}$]dec-5-yl methane sulphate, (1S,3S,4S,8R)-3-(3,4-Dichlorophenyl)-5-methoxy-7-azatricyclo[5.3.0.0$^{4,8}$]decane, (1S,3S,4S,8R)-3-(3,4-Dichlorophenyl)-5-ethoxy-7-azatricyclo[5.3.0.0$^{4,8}$]decane, (1S,3S,4S,8R)-3-(4-chlorophenyl)-7-azatricyclo[5.3.0.0$^{4,8}$]decan-5-one, (1S,3S,4S,8R)-3-(4-chlorophenyl)-7-azatricyclo[5.3.0.0$^{4,8}$]decan-5-ol, (1S,3S,4S,8R)-3-(4-Chlorophenyl)-5-ethoxy-7-azatricyclo[5.3.0.0$^{4,8}$]decane, (1S,3S,4S,8R)-3-(3,4-Dichlorophenyl)-7-azatricyclo[5.3.0.0$^{4,8}$]decan-5-one O-benzyl-oxime, (1S,3S,4S,8R)-3-(3,4-Dichlorophenyl)-7-azatricyclo[5.3.0.0$^{4,8}$]decan-5-one O-allyl-oxime, (1S,3S,4S,8R)-3-(3,4-Dichlorophenyl)-7-azatricyclo[5.3.0.0$^{4,8}$]decan-5-one oxime, (1S,3S,4S,8R)-3-(3,4-Dichlorophenyl)-7-azatricyclo[5.3.0.0$^{4,8}$]decan-5-one O-tert.-butyl-oxime, (1S,3S,4S,8R)-3-(3,4-Dichlorophenyl)-7-azatricyclo[5.3.0.0$^{4,8}$]decan-5-one O-ethyl-oxime, (1S,3S,4S,8R)-5-Allyloxy-3-(3,4-dichlorophenyl)-7-azatricyclo[5.3.0.0$^{4,8}$]decane, Ethyl(1S,3S,4S,8R)-2-[3-(3,4-dichlorophenyl)-7-azatricyclo[5.3.0.0$^{4,8}$]dec-5-yliden]acetate, (1S,3S,4S,8R)-3-(4-chlorophenyl)-7-azatricyclo[5.3.0.0$^{4,8}$]decan-5-one oxime, N1-[1S,3S,4S,8R)-3-(4-chlorophenyl)-7-azatricyclo[5.3.0.0$^{4,8}$]dec-5-yl]acetamide, or (1S,3S,4S,8R)-3-(3,4-Dichlorophenyl)-7-azatricyclo[5.3.0.0$^{4,8}$]dec-5-yl amine or a pharmaceutically acceptable addition salt thereof;

a pharmaceutical composition, comprising an effective amount of a compound as any above together with at least one pharmaceutically acceptable carrier or diluent;

the use of a compound as any above for the manufacture of a medicament for the treatment of a disorder or disease of a living animal body, including a human, which disorder or disease is responsive to the inhibition of monoamine neurotransmitter reuptake in the central nervous system;

the use of a compound as any above for the manufacture of a medicament for the treatment of a disorder or disease of a living animal body, including a human, which disorder or disease is responsive to the inhibition of serotonine reuptake in the central nervous system;

the use of a compound as any above for the manufacture of a medicament for the treatment of depression and related disorders such as pseudodementia or Ganser's syndrome, obsessive compulsive disorders, panic disorders, memory deficits, attention deficit hyperactivity disorder, obesity, anxiety and eating disorders;

the use as any above, wherein the compound employed is (1S,2S,4S,7R)-2-(3,4-Dichlorophenyl)-8-azatricyclo[5.4.0.0$^{4,8}$]undecan-11-one, (1S,2S,4S,7R)-2-(3,4-Dichlorophenyl)-8-azatricyclo[5.4.0.0$^{4,8}$]undecan-11-ol, (1S,3S,4S,8R)-3-(3,4-Dichlorophenyl)-7-azatricyclo[5.3.0.0$^{4,8}$]decan-5-one, (1S,3S,4S,8R)-3-(3,4-Dichlorophenyl)-7-azatricyclo[5.3.0.0$^{4,8}$]decan-5-one O-methyl-oxime, (1S,2S,4S,7R)-2-(4-Chlorophenyl)-8-aza-tricyclo[5.4.0.0$^{4,8}$]undecan-11-one, (1S,3S,4S,8R)-3-(3,4-Dichlorophenyl)-7-azatricyclo[5.3.0.0$^{4,8}$]decan-5-ol, (1S,3S,4S,8R)-3-(3,4-Dichlorophenyl)-7-azatricyclo[5.3.0.0$^{4,8}$]dec-5-yl acetate, (1S,3S,4S,8R)-3-(3,4-Dichlorophenyl)-7-azatricyclo[5.3.0.0$^{4,8}$]dec-5-yl methane sulphate, (1S,3S,4S,8R)-3-(3,4-Dichlorophenyl)-5-methoxy-7-azatricyclo[5.3.0.0$^{4,8}$]decane, (1S,3S,4S,8R)-3-(3,4-Dichlorophenyl)-5-ethoxy-7-azatricyclo[5.3.0.0$^{4,8}$]decane,
(1S,3S,4S,8R)-3-(4-chlorophenyl)-7-azatricyclo[5.3.0.0$^{4,8}$]decan-5-one,
(1S,3S,4S,8R)-3-(4-chlorophenyl)-7-azatricyclo[5.3.0.0$^{4,8}$]decan-5-ol,
(1S,3S,4S,8R)-3-(4-Chlorophenyl)-5-ethoxy-7-azatricyclo[5.3.0.0$^{4,8}$]decane,
(1S,3S,4S,8R)-3-(3,4-Dichlorophenyl)-7-azatricyclo[5.3.0.0$^{4,8}$]decan-5-one O-benzyl-oxime,
(1S,3S,4S,8R)-3-(3,4-Dichlorophenyl)-7-azatricyclo[5.3.0.0$^{4,8}$]decan-5-one O-allyl-oxime,
(1S,3S,4S,8R)-3-(3,4-Dichlorophenyl)-7-azatricyclo[5.3.0.0$^{4,8}$]decan-5-one oxime,
(1S,3S,4S,8R)-3-(3,4-Dichlorophenyl)-7-azatricyclo[5.3.0.0$^{4,8}$]decan-5-one O-tert.-butyl-oxime,
(1S,3S,4S,8R)-3-(3,4-Dichlorophenyl)-7-azatricyclo[5.3.0.0$^{4,8}$]decan-5-one O-ethyl-oxime,
(1S,3S,4S,8R)-5-Allyloxy-3-(3,4-dichlorophenyl)-7-azatricyclo[5.3.0.0$^{4,8}$]decane,
Ethyl(1S,3S,4S,8R)-2-[3-(3,4-dichlorophenyl)-7-azatricyclo[5.3.0.0$^{4,8}$]dec-5-yliden]acetate,
(1S,3S,4S,8R)-3-(4-chlorophenyl)-7-azatricyclo[5.3.0.0$^{4,8}$]decan-5-one oxime,
N1-[1S,3S,4S,8R)-3-(4-chlorophenyl)-7-azatricyclo[5.3.0.0$^{4,8}$]dec-5-yl]acetamide, or
(1S,3S,4S,8R)-3-(3,4-Dichlorophenyl)-7-azatricyclo[5.3.0.0$^{4,8}$]dec-5-yl amine
or a pharmaceutically acceptable addition salt thereof;

a method of treating a disorder or disease of a living animal body, including a human, which disorder or disease is responsive to the inhibition of monoamine neurotransmitter re-uptake, comprising the step of administering to such a living animal body, including a human, in need thereof a therapeutically effective amount of a compound as any above;

a method of treating a disorder or disease of a living animal body, including a human, which disorder or disease is responsive to the inhibition of serotonin re-uptake, comprising the step of administering to such a living animal body, including a human, in need thereof a therapeutically effective amount of a compound as any above;

the method as any above wherein depression and related disorders such as pseudodementia or Ganser's syndrome, obsessive compulsive disorders, panic disorders, memory deficits, attention deficit hyperactivity disorder, obesity, anxiety and eating disorders are treated; and a method for the preparation of the compounds as above comprising forming a fused tropane ring having the formula

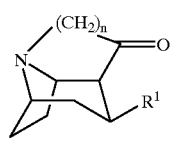

wherein n and R$^1$ is as defined in claim 1, by ring-closure of a compound having the formula

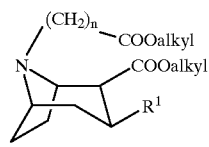

wherein n and R$^1$ is as defined in claim 1 and thereafter optionally converting the compound obtained to another compound of the invention using conventional methods, and/or optionally forming a pharmaceutically acceptable salt thereof.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, or 1,2-, 2,3-, or 3,4-butenyl.

Alkynyl means a group of from two to six carbon atoms, including at least one triple bond, for example, but not limited to ethynyl, 1,2-, 2,3-propynyl, or 1,2-, 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Cycloalkoxy is O-cycloalkyl, wherein cycloalkyl is as defined above.

Amino is NH$_2$ or NH-alkyl or N-(alkyl)$_2$, wherein alkyl is as defined above.

Aryl is an aromatic hydrocarbon, such as phenyl or naphthyl.

I.p. means intraperetoneally, which is a well known route of administration.

P.o. means peroral, which is a well known route of administration.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that some compounds of the present invention contain chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or I-(tartrates, mandelates, or camphorsulphonate) salts for example.

The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

The following scheme illustrates one method by which the compounds of the invention can be prepared:

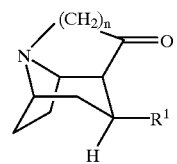

The substituents R and R″ means alkyl, Hal is halogen and n and $R^1$ is as defined above.

The processes in the reaction scheme above is carried out in conventional manner.

Compounds of the invention wherein X and Y together forms =O or where one of X and Y is OH and the other is hydrogen can be converted to other compounds of the invention using conventional methods, as illustrated in the following reaction schemes:

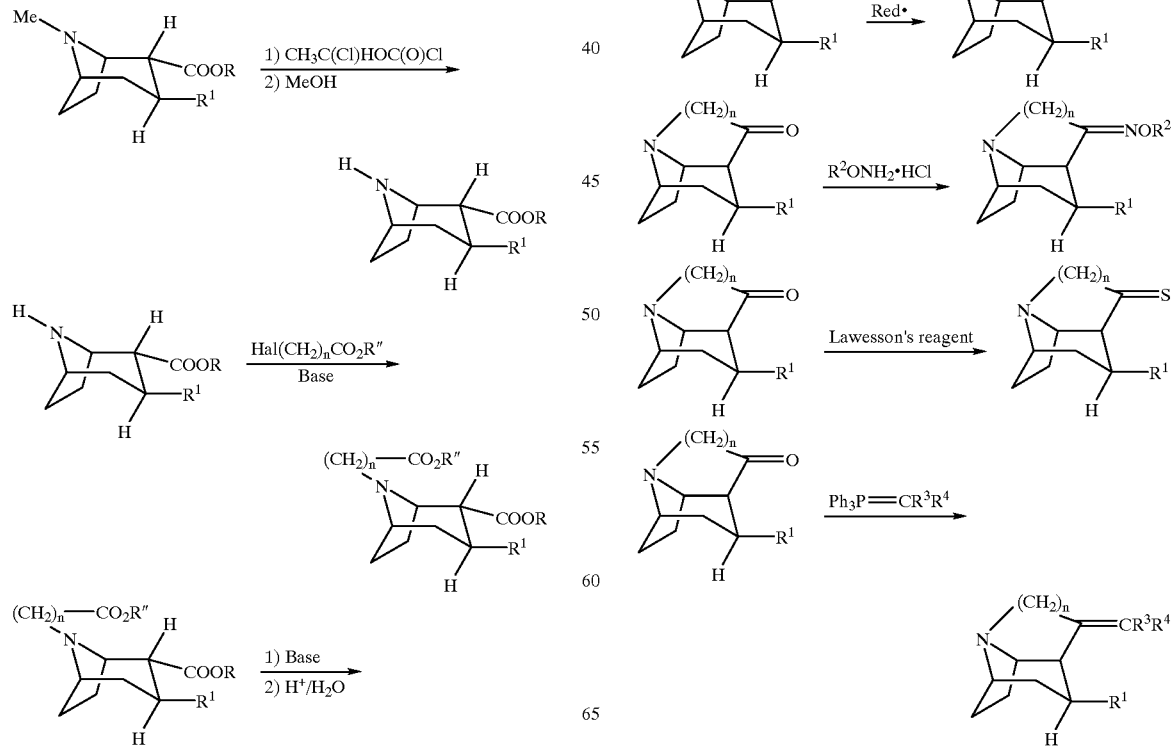

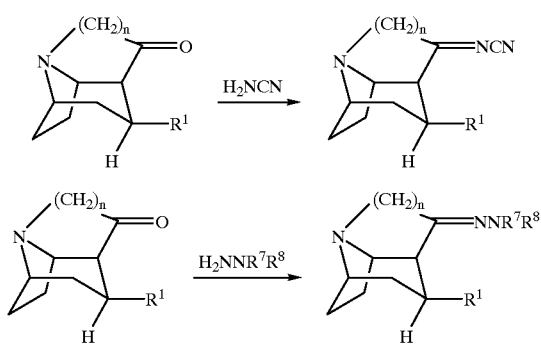

In the reaction scheme above W', W", $R^1$, $R^2$, $R^3$, $R^4$, $R^7$, $R^8$, n and p is as defined above.

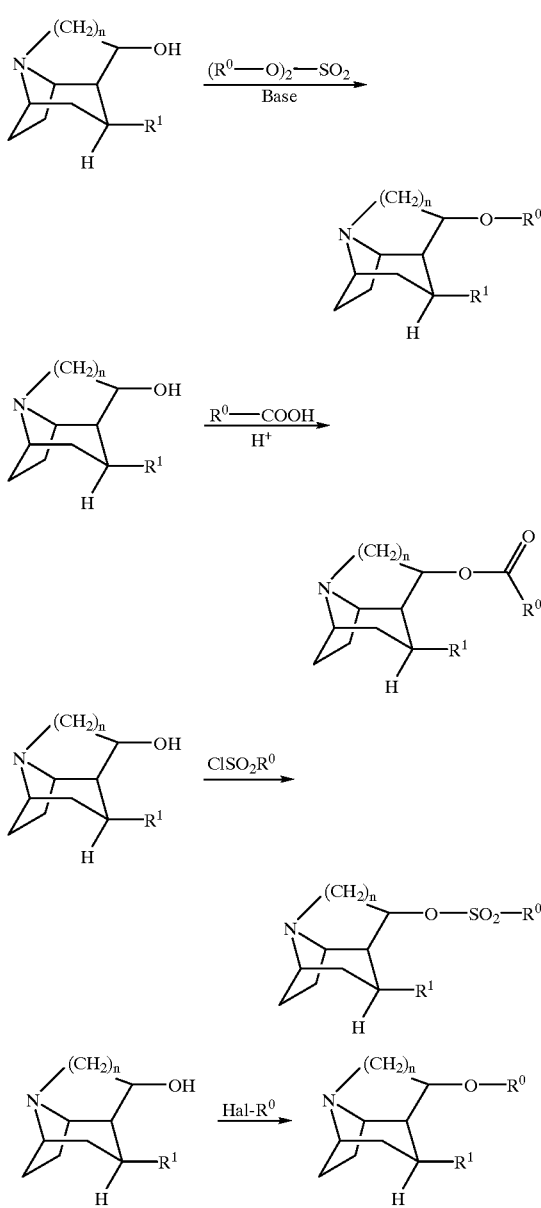

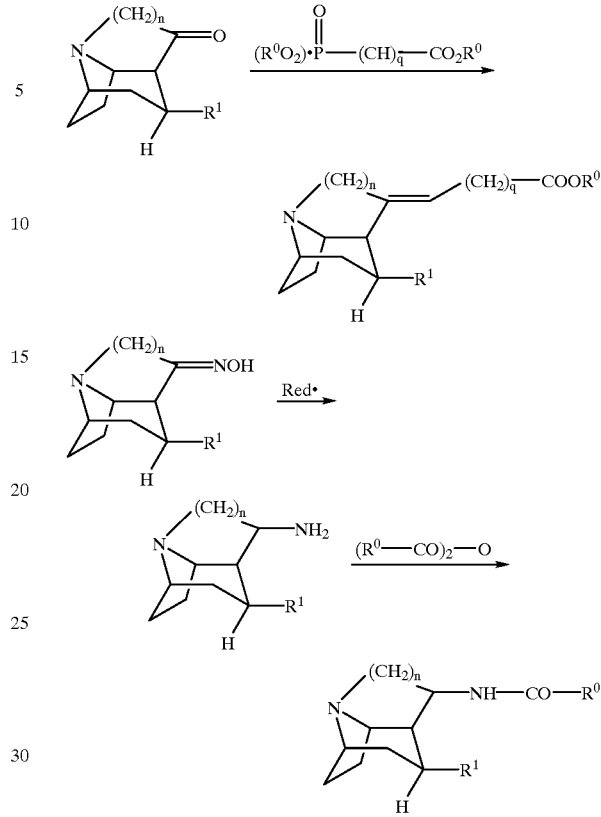

In the above reaction schemes $R^o$ is alkyl, cycloalkyl, cycloalkylalkyl, alkenyl, alkynyl, aryl and arylalkyl and n and $R^1$ is as defined above.

The processes in the above reaction schemes are carried out in conventional manner.

Starting materials for the processes described in the present patent application are known or can be prepared by known processes from commercially available materials, see for example U.S. patent application Ser. No. 5,444,070.

The products of the reactions described herein are isolated by conventional means such as extraction, crystallization, distillation, chromatography, and the like.

Biology

The compounds of the invention have been tested for their ability to inhibit reuptake of dopamine(DA) noradrenaline (NA) and serotonine(5-HT) in synaptosomes.

Background

Specific neurotransmitter transporters/uptake sites on nerve terminals presumably function to terminate neuronal signaling by removing the neurotransmitters dopamine, noradrenaline and serotonine, respectively, from the synaptic cleft. The activity of the transporter integral proteins can be measured in vitro by synaptosomal uptake of $^3$H-dopamine, $^3$H-noradrenaline and $^3$H-serotonine, respectively.

In Vitro Inhibition of $^3$H-dopamine ($^3$H-DA) Uptake in Striatal Synaptosomes Tissue preparations: Preparations are performed at 0–4° C. unless otherwise indicated. Corpi striati from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-DA (1 nM, final concentration), mixed and incubated for 25 min at 37° C. Non-specific uptake is determined using benztropine (10 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-DA by 50%).

In Vitro Inhibition of $^3$H-noradrenaline ($^3$H-NA) Uptake in Hippocampal Synaptosomes Tissue preparation: Preparations are performed at 0–4° C. unless otherwise indicated. Hippocampi from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (2000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 0.97 mM $CaCl_2$, 10 mM glucose and 1 mM ascorbic acid.

Assay: Aliquots of 4.0 ml tissue suspension are added to 100 μl of test solution and 100 μl of $^3$H-NA (1 nM, final concentration), mixed and incubated for 90 min at 37° C. Non-specific uptake is determined using desipramine (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-NA by 50%).

In Vitro Inhibition of $^3$H-5-hydroxytryptamine ($^3$H-5-HT, Serotonin) Uptake in Cortical Synaptosomes Tissue preparation: Preparations are performed at 0–4° C. unless otherwise indicated. Cerebral cortices from male Wistar rats (150–200 g) are homogenized for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 μl of test solution and 100 μl of $^3$H-5-HT (1 nM, final concentration), mixed and incubated for 30 min at 37° C. Non-specific uptake is determined using citalopram (1 μM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (μM) of the test substance which inhibits the specific binding of $^3$H-5-HT by 50%).

Test results obtained by testing selected compounds of the present invention appear from the below table:

TABLE 1

| Test compound | DA-uptake $IC_{50}$ (μM) | NA-uptake $IC_{50}$ (μM) | 5-HT-uptake $IC_{50}$ (μM) |
|---|---|---|---|
| (1S,2S,4S,7R)-2-(3,4-Dichloro-phenyl)-8-azatricyclo[5.4.0.0$^{4,8}$]-undecan-11-one O-methyl-oxime | 0.0120 | 0.0020 | 0.0033 |
| (1S,2S,4S,7R)-2-(3,4-Dichloro-phenyl)-8-azatricyclo[5.4.0.0$^{4,8}$]-undecan-11-one | 0.18 | 0.0350 | 0.0075 |
| (1S,3S,4S,8R)-3-(3,4-Dichloro-phenyl)-7-azatricyclo[5.3.0.0$^{4,8}$]-decan-5-one O-methyl-oxime | 0.0160 | 0.0009 | 0.0032 |
| (1S,2S,4S,7R)-2-(3,4-Dichloro-phenyl)-8-azatricyclo[5.4.0.0$^{4,8}$]-undecan-11-ol | 0.0750 | 0.0041 | 0.0028 |
| (1S,3S,4S,8R)-3-(3,4-Dichloro-phenyl)-7-azatricyclo[5.3.0.0$^{4,8}$]-decan-5-one | 0.12 | 0.0052 | 0.0026 |
| (1S,3S,4S,8R)-3-(3,4-Dichloro-phenyl)-7-azatricyclo[5.3.0.0$^{4,8}$]-decan-5-ol | 0.25 | 0.0074 | 0.0018 |
| (1S,3S,4S,8R)-3-(3,4-Dichloro-phenyl)-7-azatricyclo[5.3.0.0$^{4,8}$] dec-5-yl acetate | 0.21 | 0.0061 | 0.0075 |
| (1S,3S,4S,8R)-3-(3,4-Dichlorophenyl)-5-methoxy-7-azatricyclo[5.3.0.0$^{4,8}$]decane | 0.022 | 0.0014 | 0.0001 |

The results presented above show that the compounds tested efficiently inhibits reuptake of dopamine, noradrenaline and serotonine in synaptosomes.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such a s a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of the present invention are extremely useful in the treatment of depression and related disorders due to their serotonin, noradrenaline and dopamine uptake-inhibiting activity together with their low degree of undesired side-effects. These properties also make the compounds of this invention extremely useful in the treatment of obsessive compulsive disorders, panic disorders, memory deficits, attention deficit hyperactivity disorders, obesity, anxiety and eating disorders as well as other disorders sensitive to the serotonin, noradrenaline and dopamine uptake-inhibiting activity of the compounds of the present invention. The compounds of this invention may accordingly be administered to a living animal body, including a human, in need of treatment, alleviation, or elimination of an indication associated with or responsive to dopamine, noradrenaline and serotonine uptake-inhibiting activity.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

Example 1

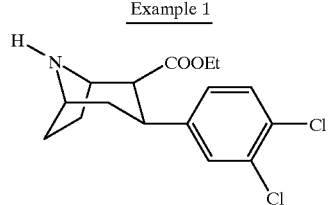

(1,2R,3S,5S)-3-(3,4-Dichlorophenyl)-8-azabicyclo[3.2.1] octane-2-carboxylic acid ethyl ester (2b)

(1R,2R,3S,5S)-3-(3,4-Dichlorophenyl)-8-methyl-8-azabicyclo[3.2.1]octane-2-carboxylic acid ethyl ester (1b) (17.9 g) was dissolved in 100 ml dry 1,2-dichloroethane and added 1-chloroethyl chloroformate (7.5 ml). The reaction mixture was refluxed for 3 hours, and then evaporated to an oil. The oil was dissolved in methanol, and the solution was refluxed for 14 hours and evaporated to an oil. The oil was dissolved in water, conc. ammonia (aq) was added until pH=10, the water phase was extracted with ether, that was dried with magnesium sulphate and evaporated to an oil. Yield 18.7 g (107%).

Example 2

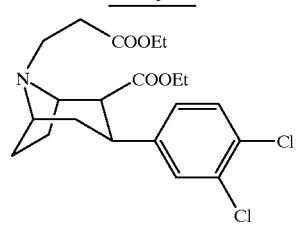

(1R,2R,3S,5S)-3-(3,4-Dichlorophenyl)-8-(2-ethoxycarbonyl ethyl)-8-azabicyclo[3.2.1]octane-2-carboxylic acid ethyl ester (3b)

(1R,2R,3S,5S)-3-(3,4-Dichlorophenyl)-8-azabicyclo [3.2.1]octane-2-carboxylic acid ethyl ester (2b) (8.3 g) was dissolved in dimethylsulfoxide (40 ml) and added potassium hydroxide (5.6 g) and ethyl 3-bromopropionate (3.8 ml). The reaction mixture was stirred at room temperature overnight, and poured into 200 ml water, this solution was washed with ether, that was dried with magnesium sulphate and evaporated to an oil. Yield 8.5 g (80%), MS m/z 427+429.

Example 3

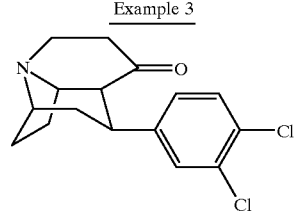

(1S,2S,4S,7R)-2-(3,4-Dichlorophenyl)-8-azatricyclo [5.4.0.0$^{4,8}$]undecan-11-one (4)

(1R,2R,3S,5S)-3-(3,4-Dichlorophenyl)-8-(ethoxycarbonyl ethyl)-8-aza-bicyclo[3.2.1]octane-2-carboxylic acid ethyl ester (3b) (8.5 g) was dissolved in dry toluene and added sodium hydride (0.5 g) (60% disp. in oil). The reaction mixture was refluxed for half an hour, and then evaporated to an oil, this was dissolved in 10 M HCl (aq), this solution was refluxed for 16 hours and then cooled to room temperature and added 12 M NaOH (aq) until pH=12. This solution was washed with ether, that was dried with magnesium sulphate and evaporated to an oil. Yield 1.9 g (31%) GC/MS 96% pure M=309+311.

Example 4

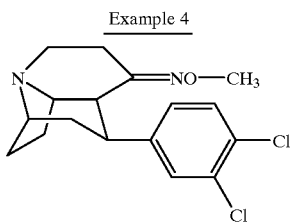

(1S,2S,4S,7R)-2-(3,4-Dichlorophenyl)-8-azatricyclo[5.4.0.0$^{4,8}$]undecan-11-one O-methyl-oxime (5)

(1S,2S,4S,7R)-2-(3,4-Dichlorophenyl)-8-aza-tricyclo[5.4.0.0$^{4,8}$]undecan-11-one (4) (1.4 g) was dissolved in methanol and methoxylamine hydrochloride (0.6 g) and potassium carbonate (1.4 g) was added. This suspension was stirred at room temperature for 16 hours, and then evaporated to an oil, this was dissolved in 1 M HCl and washed with ether. The water phase was added 12 M NaOH until pH=12 and extracted with ether. The organic phase was dried with magnesium sulphate and evaporated to an oil. Yield 0.2 g MS: m/z 338 (M$^+$, 80), 340 (M$^+$ +2, 51), 342 (M$^+$+4, 8).

Example 5

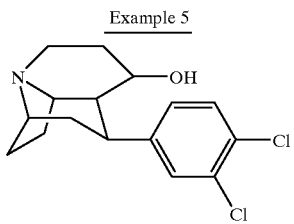

(1S,2S,4S,7R)-2-(3,4-Dichlorophenyl)-8-azatricyclo[5.4.0.0$^{4,8}$]undecan-11-ol (6)

(1S,2S,4S,7R)-2-(3,4-Dichlorophenyl)-8-azatricyclo[5.4.0.0$^{4,8}$]undecan-11-one (4) (0.5 g) was dissolved in methanol (10 ml) and added sodium borohydride (0.2 g). The reaction mixture was stirred at room temperature for 2 hours, then added water (0.5 ml) and evaporated to an oil. The oil was added ethyl acetate (10 ml) and 1 M sodium hydroxide (aq.) (10 ml), the organic phase was dried with magnesium sulphate and evaporated to an oil. The oil was purified by flash chromatography on silica gel, and eluted with dichloromethane/methanol/25% ammonia (aq.) (89/10/1 v/v). The product fractions was evaporated to a foam. Yield 200 mg (40%). MS(EI+): m/z 311(M$^+$, 100), 313 (M$^+$+2, 68), 315 (M$^+$+4, 12).

(1S,2S,4S,7R,11R)-2-(3,4-Dichlorophenyl)-8-azatricyclo[5.4.0.0$^{4,8}$]undecan-11-ol (6a)

The title compound was prepared in the same manner as (6), but purified by chromatography over silica gel (dichloromethane/acetone/methyl alcohol (4/1/1)). Yield 0.2 g (18%) as white crystals MP 185.6–186.9° C.

Example 6

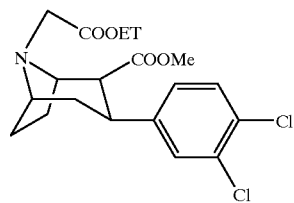

(1R,2R,3S,5S)-3-(3,4-Dichlorophenyl)-8-(ethoxycarbonyl methyl)-8 -azabicyclo[3.2.1]octane-2-carboxylic acid methyl ester (7)

(1R,2R,3S,5S)-3-(3,4-Dichlorophenyl)-8-methyl-8-azabicyclo[3.2.1]octane-2-carboxylic acid methyl ester (1a) (19.4 g) in dry 1,2-dichloroethane (125 ml) was added 1-chloroethyl chloroformate (10 ml). The reaction mixture was refluxed for 16 hours, then left at room temperature for 48 hours and then evaporated to an oil. The oil was dissolved in methanol (125 ml) and refluxed for 45 minutes, then evaporated to an oil. The oil was dissolved in water, and added conc. ammonia (aq) until pH=10, the water phase was extracted with ether, the organic phase was dried with magnesium sulphate and evaporated to an oil. The oil was dissolved in absolute ethanol (180 ml) and added ethyl bromoacetate (7.7 ml) and potassium carbonate (10.2 g). The reaction mixture was refluxed for 2 hours, then stirred overnight at room temperature and evaporated to an oil. The oil was added water (0.5 l) and extracted with ether (2×300 ml), the combined ether phases was dried with magnesium sulphate and evaporated to and oil. The oil was purified by flash chromatography on silica gel 60 (400 g) and eluted with ethyl acetate and petroleum ether (1:1), the product fractions was evaporated to an oil. Yield 10 g (42%) MS(EI+): m/z 399 (M$^+$, 12), 401 (M$^+$+2, 7), 403 (M$^+$+4, 2).

Example 7

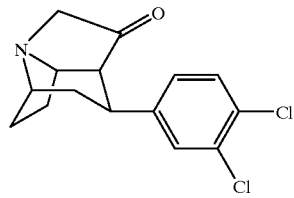

(1S,3S,4S,8R)-3-(3,4-Dichlorophenyl)-7-azatricyclo[5.3.0.0$^{4,8}$]decan-5-one (8)

(1R,2R,3S,5S)-3-(3,4-Dichlorophenyl)-8-(ethoxycarbonyl methyl)-8-azabicyclo[3.2.1]octane-2-carboxylic acid methyl ester (7) (22.4 g) in xylene (200 ml) was added 1 M sodium ethoxide in ethanol (63 ml). The solution was distilled until the temperature reached 138° C., when refluxed for 90 minutes. The reaction mixture was added water (50 ml) and conc. hydrochloric acid (15 ml) and refluxed for 16 hours. The reaction mixture was added water (200 ml) and xylene was removed by azeotrope distillation with water, occasionally water was added to maintain the volume of the solution. The residue was added water to a total volume of 0.5 l, conc. ammonia (aq) was added until pH=10 and the product precipitated, after filtration the precipitate was washed with ether (50 ml). Yield 13 g (78%) MP 176–182° C.

Example 8

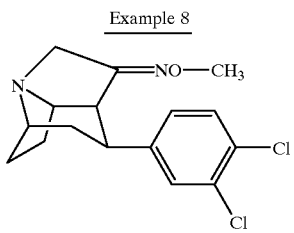

(1S,3S,4S,8R)-3-(3,4-Dichlorophenyl)-7-azatricyclo[5.3.0.0$^{4,8}$]decan-5-one O-methyl-oxime (9)

(1S,3S,4S,8R)-3-(3,4-Dichlorophenyl)-7-azatricyclo[5.3.0.0$^{4,8}$]decan-5-one (8) (0.29 g) and methoxylamine hydrochloride (0.09 g) was dissolved in absolute ethanol (50 ml). The reaction mixture was refluxed for 4 hours and then evaporated to an oil. The oil was suspended in water (50 ml) and added conc. ammonia (aq.) until pH=10 and then extracted with ether. The ether phase was dried with magnesium sulphate and evaporated to an oil. The residue was dissolved in absolute ethanol and then added 0.4 M fumaric acid in absolute ethanol (1.9 ml), the solution was evaporated to a foam. Yield 0.29 g (66%). MP 143–146° C.

Example 9

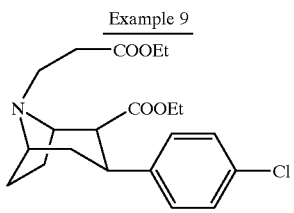

(1R,2R,3S,5S)-3-(4-Chlorophenyl)-8-(ethoxycarbonyl ethyl)-8-aza-bicyclo[3.2.1]octane-2-carboxylic acid methyl ester (11)

(1S,2S,4S,7R)-2-(4-Chlorophenyl)-8-methyl-8-azabicyclo[3.2.1]octane-2-carboxylic acid methyl ester (1c) (23 g) was dissolved in dry 1,2-dichloroethane (100 ml) and added 1-chloroethyl chloroformate (12 g). The reaction mixture was refluxed for 4.5 hours and then evaporated to an oil. The residue was dissolved in methanol (100 ml) and refluxed for 1 hour. The reaction mixture was evaporated to an oil, this was dissolved in water and added 25% ammonia (aq.) until pH=10, this solution was extracted with ether, that was washed with water and dried with magnesium sulphate and evaporated to an oil, that crystallised upon standing at room temperature. The solid was dissolved in absolute ethanol (200 ml) and added potassium carbonate (15 g) and ethyl 3-bromopropionate (12 ml), the reaction mixture was refluxed for 3 hours and then evaporated to an oil, this was added ether and water. The ether phase was washed with water and dried with magnesium sulphate and evaporated to an oil. The oil was purified by flash chromatography on silica gel (300 g) and eluted with ethyl acetate. The product fractions was evaporated to an oil. Yield 24 g (80%) MS(EI+): m/z 379 (M$^+$, 52), 381 (M$^+$+2, 17), 383 (M$^+$+4, 2).

Example 10

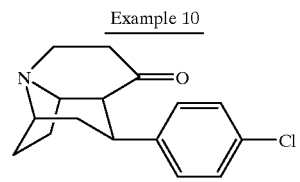

(1S,2S,4S,7R)-2-(4-Chlorophenyl)-8-azatricyclo[5.4.0.0$^{4,8}$]undecan-11-one (12)

(1R,2R,3S,5S)-3-(4-Chlorophenyl)-8-(ethoxycarbonyl methyl)-8-azabicyclo[3.2.1]octane-2-carboxylic acid methyl ester (10) (3.15 g) was dissolved in dry xylene (20 ml) and added sodium hydride (0.35 g 60% disp. in oil), the reaction mixture was refluxed for 4 hours and then cooled to room temperature and added crushed ice and 4 N hydrochloric acid (15 ml). Then the ice was melted the phases were separated, the water phase were washed with ether (2×50 ml) and added conc. ammonia (aq.) until pH=10, and extracted with dichloromethane. The organic phase was washed with brine and dried with magnesium sulphate and evaporated to an oil. The oil was added conc. hydrochloric acid (20 ml) and ethanol (96%) until everything was in solution, the reaction mixture was refluxed for 16 hours, the reaction mixture was cooled to room temperature and added crushed ice and added conc. ammonia (aq.) until pH=10 and then extracted with dichloromethane, the organic phase was dried with magnesium sulphate and evaporated to an oil, this was crystallised from ethanol (96%). Yield 0.24 g (11%) MP 156.5–157.7° C.

Example 11

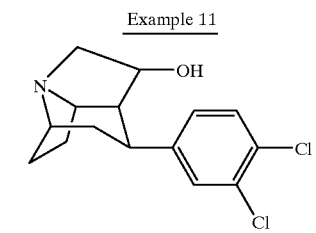

(1S,3S,4S,8R)-3-(3,4-Dichlorophenyl)-7-azatricyclo[5.3.0.0$^{4,8}$]decan-5-ol (13)

(1S,3S,4S,8R)-3-(3,4-Dichlorophenyl)-7-azatricyclo[5.3.0.0$^{4,8}$]decan-5-one (8) (1 g) was dissolved in methanol and added sodium borohydride (0.26 g). The reaction mixture was stirred at room temperature for 30 minutes, then added water (0.5 ml) and evaporated to dryness. the residue was added ethyl acetate (200 ml)and 1 M sodium hydroxide (aq.) (50 ml), the organic phase was dried with magnesium sulphate and evaporated to a foam. Yield 0.67 g (66%) MP 203–205° C.

Fumarate: The title compound (7. g b, 25.5 mmol) was dissolved in methyl alcohol and added fumaric acid (3 g, 16 mmol) in methyl alcohol and was heated at reflux until a the solution was clear, the fumarate salt of the title compound precipitated then the solution was cooled on an ice/water bath, the crystals was recrystalised form absolute ethyl alcohol (150 mL) and water (46 mL). Yield 5.42 g MP 250.5–251° C.

Example 12

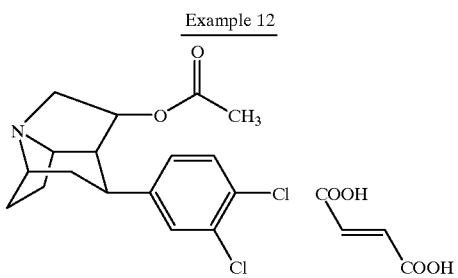

(1S,3S,4S,8R)-3-(3,4-Dichlorophenyl)-7-azatricyclo[5.3.0.0$^{4,8}$]dec-5-yl acetate fumarate(14)

(1S,3S,4S,8R)-3-(3,4-Dichlorophenyl)-7-azatricyclo[5.3.0.0$^{4,8}$]decan-5-ol (13) (1 g, 3.3 mmol) was dissolved in glacial acetic acid (5 mL) and added concentrated hydrochloric acid (5 mL), the reaction mixture was heated at reflux for 90 minutes then cooled to room temperature and added 25% aqueous ammonia until pH=9.5, the water phase was extracted with diethyl ether. The ether phase was concentrated to an oil, the residue was chromatographed over silica gel (dichloromethane/acetone/methyl alcohol 4/1/1). The product fractions was concentrated to an oil, the oil was dissolved in diethyl ether/methyl alcohol and added a solution of fumaric acid (0.14 g, 1.2 mmol) in methyl alcohol, where upon white crystals precipitated, the product was isolated by filtration. Yield 0.36 g (24%) MP 214–216° C.

Example 13

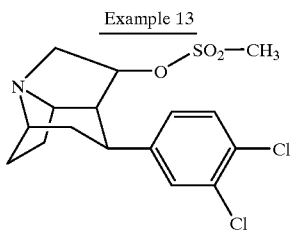

(1S,3S,4S,8R)-3-(3,4-Dichlorophenyl)-7-azatricyclo[5.3.0.0$^{4,8}$]dec-5-yl methane sulphate (15)

(1S,3S,4S,8R)-3-(3,4-Dichlorophenyl)-7-azatricyclo[5.3.0.0$^{4,8}$]decan-5-ol (13) (1 g, 3.3 mmol) was dissolved in dichloromethane (150 mL) and added methanesulfonyl chloride (0.3 mL, 3.7 mmol) and triethylamine (1.6 mL, 12 mmol). The reaction mixture was stirred at room temperature under a nitrogen atmosphere for one hour then concentrated to an oil. The oil was added 4 M NaOH and dichloromethane, the organic phase was dried (magnesium sulphate) and concentrated to a foam. Yield 0.61 g (48%) MP 139–141° C.

Example 14

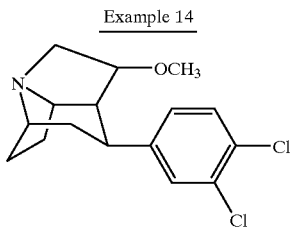

(1S,3S,4S,8R)-3-(3,4-Dichlorophenyl)-5-methoxy-7-azatricyclo[5.3.0.0$^{4,8}$]decane (16)

(1S,3S,4S,8R)-3-(3,4-Dichlorophenyl)-7-azatricyclo[5.3.0.0$^{4,8}$]decan-5-ol (1.3 g, 4.4 mmol) was dissolved in anhydrous tetrahydrofuran (30 mL) and added potassium tert.-butoxide (1.54 g, 13.8 mmol), the reaction mixture was stirred at room temperature under a nitrogen atmosphere for 45 minutes then cooled to –70° C., dimethylsulphate (4.3 mL, 1M in anhydrous tetrahydrofuran, 4.3 mmol) was added in such rate that the temperature didn't exceed –65° C., the reaction mixture was stirred at this temperature for one hour then allowed to warm up to room temperature and added water (50 mL) then extrated with diethyl ether (3×50 mL). The organic phase was dried (sodium sulphate) and concentrated to an oil, this oil crystallised upon standing at room temperature. Yield 0.32 g (24%) MP 119.2–120.3° C.

Example 15

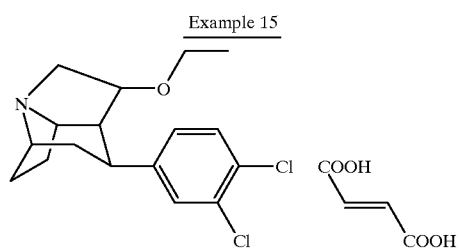

(1S,3S,4S,8R)-3-(3,4-Dichlorophenyl)-5-ethoxy-7-azatricyclo[5.3.0.0$^{4,8}$]decane fumarate (17)

(1S,3S,4S,8R)-3-(3,4-Dichlorophenyl)-7-azatricyclo[5.3.0.0$^{4,8}$]decan-5-ol (13) (2 g, 6.7 mmol) was dissolved in anhydrous tetrahydrofuran (40 mL) and added potassium tert.-butoxide and stirred one hour at room temperature under a nitrogen atmosphere then cooled to –70° C. and added diethylsulphate at such rate that the temperature didn't exceed –65° C. the reaction mixture was stirred at this temperature for 2 hours then allowed to warm to room temperature and added water (50 mL) and extracted with diethyl ether (3×100 mL), the organic phase was dried (magnesium sulphate) and concentrated to an oil. The oil was dissolved in methyl alcohol and added fumaric acid (0.6 g, 5.2 mmol) in methyl alcohol and the product precipitated. Yield 2 g (67%) as white crystals MP 164.1–165.9° C.

Example 16

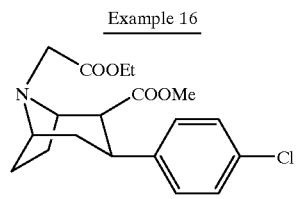

Ethyl 2-[(1R,3S,5R)-3-(4-chlorophenyl)-2-methoxycarbonyl-8-azabicyclo[3.2.1]oct-8-yl]acetate (18)

Methyl(1R,3S,5R)-3-(4-chlorophenyl)-8-azabicyclo[3.2.1]octane-2-carboxylate (10) (0.88 g, 0.31 mol) was dissolved in absolute ethyl alcohol (app. 600 mL) and added potassium carbonate (55.2 g, 0.4 mol) and ethyl bromoacetate (66.3 g, 0.4 mol), the reaction mixture was heated at reflux for 2 hours then concentrated to an oil, the residue was chromatographed over silica gel (ethyl actate), the product fractions was concentrated to an oil. Yield 98 g (87%).

Example 17

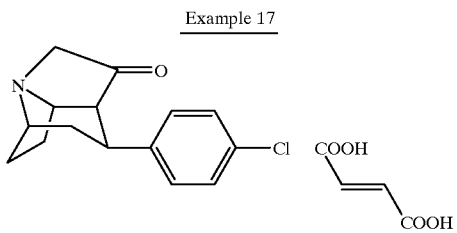

(1S,3S,4S,8R)-3-(4-chlorophenyl)-7-azatricyclo[5.3.0.0$^{4,8}$]decan-5-one fumarate (19)

Ethyl 2-[(1R,3S,5R)-3-(4-chlorophenyl)-2-methoxycarbonyl-8-azabicyclo[3.2.1]oct-8-yl]acetate (18) (42.8 g, 0.12 mol) was dissolved in toluene (400 mL), the solution was heated at reflux, with a Dean-stark trap was the solvent collected until there was no more water left, the solution was cooled to room temperature and added sodium methoxide (65 mL, a 2.1 M solution in methyl alcohol, 0.14 mol), the reaction mixture was destined until the temperature reached 100° C. then left at room temperature overnight then concentrated, the residue was added ethyl alcohol (100 mL) and concentrated to an oil, the residue was added 4 M hydrochloric acid (35 mL, 0.14 mol) and heated at reflux for 2 hours, the reaction mixture was cooled to room temperature and added 25% aqueous ammonia until pH=10, a white compound precipitated and was isolated by filtration, the solid was recrystallized from toluene (200 mL). Yield 16 g (52%) as white crystals. Some of the crystals (0.78 g, 3 mmol) was dissolved in absolute ethyl alcohol (25 mL) and added fumaric acid (0.45 g, 3.8 mmol) and absolute ethyl alcohol (5 mL), the mixture was heated until everything was dissolved then cooled to 5° C., the product precipitated and was isolated by filtration. Yield 0.99 g (88% from the free base) as beige crystals MP 205–206° C.

Example 18

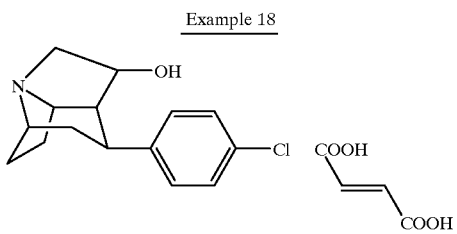

(1S,3S,4S,8R)-3-(4-chlorophenyl)-7-azatricyclo[5.3.0.0$^{4,8}$]decan-5-ol fumarate (20)

The free base of the title compound was prepared analogously to 1S,3S,4S,8R)-3-(4,3-dichlorophenyl)-7-azatricyclo[5.3.0.0$^{4,8}$]decan-5-ol. The fumarate salt was made from the free base (0.7 g, 2.7 mmol) dissolved in ethyl alcohol (10 mL, 96%) and added fumaric acid (0.35 g, 3 mmol) in ethyl alcohol (15 mL, 96%), the title compound precipitated and was isolated by filtration. Yield 0.9 g (80%) as white crystals MP 230–231° C.

Example 19

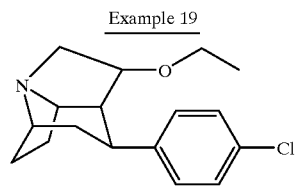

(1S,3S,4S,8R)-3-(4-Chlorophenyl)-5-ethoxy-7-azatricyclo[5.3.0.0$^{4,8}$]decane (21)

The title compound was prepared analogously to 1S,3S,4S,8R)-3-(3,4-dichlorophenyl)-5-ethoxy-7-azatricyclo[5.3.0.0$^{4,8}$]decane. Yield 0.31 g (36%) MP 72–74° C.

Example 20

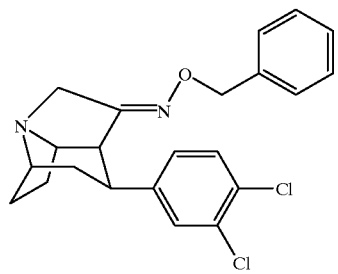

(1S,3S,4S,8R)-3-(3,4-Dichlorophenyl)-7-azatricyclo[5.3.0.0$^{4,8}$]decan-5-one O-benzyl-oxime (22)

The title compound was prepared analogously to (1S,3S,4S,8R)-3-(3,4-dichlorophenyl)-7-azatricyclo[5.3.0.0$^{4,9}$]decan-5-one O-methyl-oxime (9). Yield 0.51 g (25%) MP 125.3–126.4° C.

Example 21

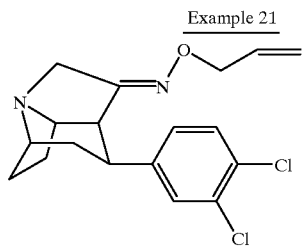

(1S,3S,4S,8R)-3-(3,4-Dichlorophenyl)-7-azatricyclo[5.3.0.0$^{4,8}$]decan-5-one O-allyl-oxime fumarate (23)

The free base of the title compound was prepared analogously to (1S,3S,4S,8R)-3-(3,4-dichlorophenyl)-7-azatricyclo[5.3.0.0$^{4,8}$]-decan-5-one O-methyl-oxime (9), the free base of the title compound (1 g, 2.8 mmol) was dissolved in ethyl alcohol and added fumaric acid (0.35 g, 3 mmol), the mixture was concentrated to a foam. Yield 0.98 g (42%) MP 45–52° C.

Example 22

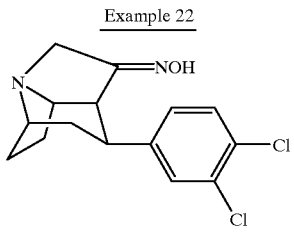

(1S,3S,4S,8R)-3-(3,4-Dichlorophenyl)-7-azatricyclo[5.3.0.0$^{4,8}$]decan-5-one oxime (24)

The title compound was prepared analogously to (1S,3S,4S,8R)-3-(3,4-dichlorophenyl)-7-azatricyclo[5.3.0.0$^{4,8}$]decan-5-one O-methyl-oxime (9). Yield 0.5 g (32%) as light brown crystals MP 143.9–144.7° C.

Example 23

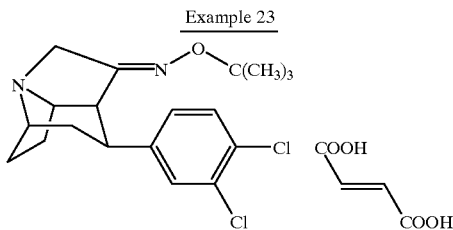

(1S,3S,4S,8R)-3-(3,4-Dichlorophenyl)-7-azatricyclo[5.3.0.0$^{4,8}$]decan-5-one O-tert.-butyl-oxime fumarate (25)

The free base of the title compound was prepared analogously to (1S,3S,4S,8R)-3-(3,4-dichlorophenyl)-7-azatricyclo[5.3.0.0$^{4,8}$]decan-5-one O-methyl-oxime (9). Yield of fumarate salt 0.51 g (21%) as light grey crystals MP 234–236° C.

Example 24

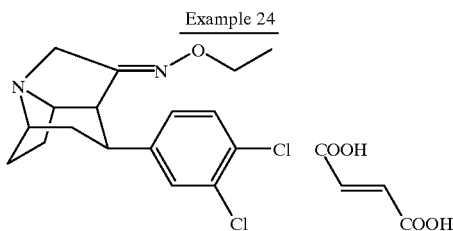

(1S,3S,4S,8R)-3-(3,4-Dichlorophenyl)-7-azatricyclo[5.3.0.0$^{4,8}$]decan-5-one O-ethyl-oxime fumarate (26)

The free base was prepared analogously to (1S,3S,4S,8R)-3-(3,4-dichlorophenyl)-7-azatricyclo[5.3.0.0$^{4,8}$]decan-5-one O-methyl-oxime (9). The free base (0.77 g, 2.3 mmol) was dissolved in methyl alcohol and added fumaric acid (0.29 g, 2.5 mmol) the mixture was concentrated to dryness. Yield 0.52 g (23%) as a light beige solid MP 62–69° C.

Example 25

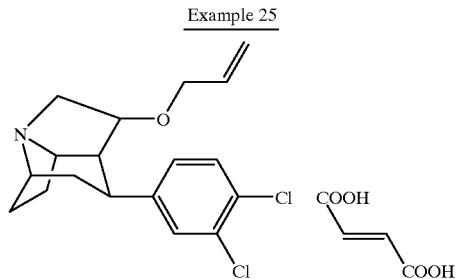

(1S,3S,4S,8R)-5-Allyloxy-3-(3,4-dichlorophenyl)-7-azatricyclo[5.3.0.0$^{4,8}$]decane fumarate (27)

(1S,3S,4S,8R)-3-(3,4-Dichlorophenyl)-7-azatricyclo[5.3.0.0$^{4,8}$]decan-5-ol (13) (2 g, 6.7 mmol) in anhydrous tetrahydrofuran (40 mL) was added potassium tert.-butoxide (2.4 g, 21 mmol) and stirred under a nitrogen atmosphere at room temperature for 90 minutes then cooled to −70° C., to this mixture was added drop by drop allyl bromide (0.8 g, 6.6 mmol), while the temperature was kept below −65° C., the reaction mixture was stirred at this temperature for 2 hours then allowed to warm up to room temperature and added water (50 mL), the mixture was extracted with diethyl ether (2×100 mL), the organic phase was dried (magnesium sulphate) and concentrated to an oil, the oil was dissolved in diethyl ether (10 mL) and added fumaric acid (0.49 g, 4.2 mmol) in methyl alcohol, the mixture was concentrated to an oil, the oil was triturated in diethyl ether, and the title compound precipitated and was isolated by filtration. Yield 1.77 g (58%) as white crystals MP 150.5–152.2° C.

Example 26

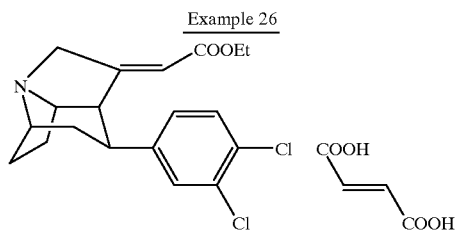

Ethyl(1S,3S,4S,8R)-2-[3-(3,4-dichlorophenyl)-7-azatricyclo[5.3.0.0$^{4,8}$]dec-5-yliden]acetate fumarate (28)

Triethyl phosphonoacetate (2.51 g, 11.2 mmol) was added drop by drop to a mixture of sodium hydride (0.5 g of a 60% dispension in mineral oil, 12 mmol) in anhydrous toluene under a nitrogen atmosphere, the mixture was stirred at room temperature for 30 minutes then added (1S,3S,4S,8R)-3-(3,4-dichlorophenyl)-7-azatricyclo[5.4.0.0$^{4,8}$]decan-5-one (8) (3.3 g, 11.1 mmol), the reaction mixture was filtered and the filtrate was concentrated, the residue was chromatographed over silica gel (dichloromethane/methyl alcohol/acetone, 4/1/1), the product fractions was concentrated to an oil, yield 1.22 g (30%). Some of the oil (0.36 g, 1 mmol) was dissolved in diethyl ether and added fumaric acid (0.13 g, 1.1 mmol) in methyl alcohol, the mixture was concentrated to an oil, the oil was stirred with diethyl ether and the title compound precipitated. Yield 0.37 g (77% from the free base) as white crystals MP 158–159° C.

Example 27

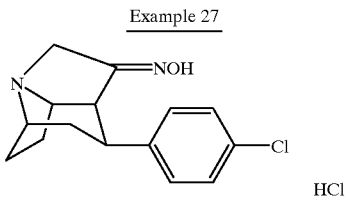

HCl (1S,3S,4S,8R)-3-(4-chlorophenyl)-7-azatricyclo[5.3.0.0$^{4,8}$] decan-5one oxime hydrochloride (29)

(1S,3S,4S,8R)-3-(4-chlorophenyl)-7-azatricyclo[5.3.0.0$^{4,}$ $_8$]decan-5-one (19) (4 g, 15.3 mmol) was dissolved in absolute ethyl alcohol (40 mL) and added hydroxylamine hydrochloride (1.3 g, 18.4 mmol), the reaction mixture was heated at reflux for 90 minutes then added more hydroxylamine hydrochloride (0.2 g, 2.9 mmol) and heated at reflux for 2 hours, the reaction mixture was stirred on an ice/water bath and the title compound precipitated and was isolated by filtration, yield 3.93 g (82%), some of the solid (1 g, 3.2 mmol) was crystallised from ethyl alcohol (approximately 25 mL) and water (approximately 5 mL). Yield 0.6 g (60% for the crystallisation) MP 284–285° C.

Example 28

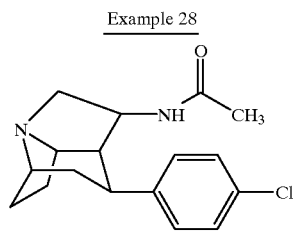

N1-[1S,3S,4S,8R)-3-(4-chlorophenyl)-7-azatricyclo [5.3.0.0$^{4,8}$]dec-5-yl]acetamide (30)

(1S,3S,4S,8R)-3-(4-chlorophenyl)-7-azatricyclo[5.3.0.0$^{4,}$ $_8$]decan-5-one oxime hydrochloride (29) (3.13 g, 10 mmol) was dissolved in methyl alcohol (300 mL) and added some Raney Nikkel (50% slurry in water), the reaction mixture was stirred under a hydrogen atmosphere for 40 hours (use of hydrogen, 0.62 L, 26 mmol), the reaction mixture was filtered though some Hyflo Super Cel U.S.A. type, the filtrate was concentrated to dryness, the residue was added water (150 mL) and 25% aqueous ammonia until pH=10, the water phase was extracted with diethyl ether (3×100 mL) and with dichloromethane (100 mL), the organic extracts was combined and dried (magnesium sulphate) and concentrated to dryness, the residue was dissolved in water (20 mL) and hydrochloric acid (5 mL, 4 M, 20 mmol) and stirred on an ice/water bath and added acetic anhydride (8.6 g, 85 mmol) and sodium acetate (8 g, 98 mmol), the reaction mixture was stirred on the ice/water bath for 2 hours, the reaction mixture was filtered, the filtrate was added 25% aqueous ammonia until pH=10 and a solid precipitated and was isolated by filtration, the precipitate was chromatographed over silica gel (dichloromethane/methyl alcohol/ acetone 4/1/1), the product fractions crystallised upon standing at room temperature. Yield 0.54 g (18%) MP 122–123.5° C.

Example 29

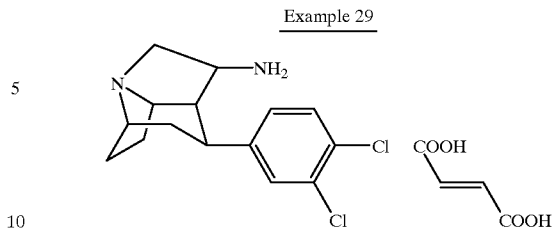

(1S,3S,4S,8R)-3-(3,4-Dichlorophenyl)-7-azatricyclo [5.3.0.0$^{4,8}$]dec-5-yl amine fumarate (31)

Sodium borohydride (0.81 g, 21.5 mmol) was suspended in anhydrous tetrahydrofuran (40 mL) and stirred under a nitrogen atmosphere and added drop by drop trifluoroacetic acid (2.45 g, 21.5 mmol) in anhydrous tetrahydrofuran (5 mL) over a period of 10 minutes then stirred at room temperature for 20 minutes, the reaction mixture was added (1S,3S,4S,8R)-3-(3,4-dichlorophenyl)-7-azatricyclo [5.3.0.0$^{4,8}$]decan-5-one O-methyl-oxime (9) (1.4 g, 4.3 mmol) in anhydrous tetrahydrofuran (5 mL) over a period of 20 minutes then stirred at room temperature for 30 minutes then heated at reflux for 2 hours, The reaction mixture was cooled to room temperature and added water (10 mL) and stirred for 1 hour then concentrated until the only solvent was water then extracted with dichloromethane (50 mL), the organic phase was dried (magnesium sulphate) concentrated to a foam yield 1.22 g (95%), some of the foam (0.5 g, 1.7 mmol) was dissolved in methyl alcohol (10 mL) and added fumaric acid (0.205 g, 1.77 mmol), the mixture was concentrated to a foam, the foam was stirred with diethyl ether and filtered, the product was dried on a filter. Yield 0.35 g (20%) MP 208–211° C.

It is claimed:

1. A compound having the formula

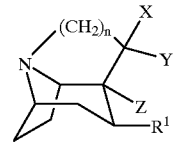

or any of its enantiomers or any mixture thereof, a pharmaceutically acceptable addition salt thereof or the N-oxide thereof wherein X and Y together form =O, =S, =NOR$^2$, =CR$^3$R$^4$, =N—CN, =N—NR$^7$R$^8$, —(CH$_2$)$_m$—, or —W'—(CH$_2$)$_p$—W"—, or one of X and Y is hydrogen and the other is —OR$^5$, —SR$^5$, or —NR$^5$R$^6$;

Z is hydrogen or —COOR$^9$;

R$^3$ and R$^4$ are independently hydrogen, halogen, alkyl, cycloalkyl, cycloalkylalkyl, alkenyl, alkynyl, alkoxy, phenyl, naphthyl, phenylalkyl, naphthylalkyl or —(CH$_2$)$_q$—COOR$^2$;

R$^2$, R$^5$ and R$^6$ are independently hydrogen, alkyl, cycloalkyl, cycloalkylalkyl, alkenyl, alkynyl, phenyl, naphthyl, or phenylalkyl, naphthylalkyl, —CO-alkyl, or —SO$_2$-alkyl;

R$^7$ and R$^8$ are independently hydrogen, alkyl, cycloalkyl, cycloalkylalkyl, alkenyl, alkynyl, phenyl, naphthyl, or phenylalkyl, naphthylalkyl;

R$^9$ is alkyl, alkenyl or alkynyl;

R$^1$ is alkyl, alkenyl, alkynyl, phenyl, naphthyl, or phenylalkyl, naphthylalkyl;

where said phenyl and naphthyl groups may be substituted one or more times with substituents selected from the group consisting of halogen, $CF_3$, CN, alkoxy, cycloalkoxy, alkyl, cycloalkyl, alkenyl, alkynyl, $NH_2$, NH-alkyl, N-(alkyl)$_2$ and nitro;

W' and W" are each independently O or S;

n is 1, 2, 3, or 4;

m is 2, 3, 4, or 5;

p is 1, 2, 3, 4, or 5; and q is 0, 1, 2, 3, or 4.

2. The compound of claim 1, where n is 1 or 2.

3. A compound of claim 1 which is (1S,2S,4S,7R)-2-(3,4-Dichlorophenyl)-8-azatricyclo[5.4.0.0$^{4,8}$]undecan-11-one, (1S,2S,4S,7R)-2-(3,4-Dichlorophenyl)-8-azatricyclo[5.4.0.0$^{4,8}$]undecan-11-ol, (1S,3S,4S,8R)-3-(3,4-Dichlorophenyl)-7-azatricyclo[5.3.0.0$^{4,8}$]decan-5-one, (1S,3S,4S,8R)-3-(3,4-Dichlorophenyl)-7-azatricyclo[5.3.0.0$^{4,8}$]decan-5-one O-methyloxime, (1S,2S,4S,7R)-2-(4-Chlorophenyl)-8-azatricyclo[5.4.0.0$^{4,8}$]undecan-11-one, (1S,3S,4S,8R)-3-(3,4-Dichlorophenyl)-7-aza-tricyclo[5.3.0.0$^{4,8}$]decan-5-ol, (1S,3S,4S,8R)-3-(3,4-Dichlorophenyl)-7-azatricyclo[5.3.0.0$^{4,8}$]dec-5-yl acetate, (1S,3S,4S,8R)-3-(3,4-Dichlorophenyl)-7-azatricyclo[5.3.0.0$^{4,8}$]dec-5-yl methane sulfonate, (1S,3S,4S,8R)-3-(3,4-Dichlorophenyl)-5-methoxy-7-azatricyclo[5.3.0.0$^{4,8}$]decane, (1S,3S,4S,8R)-3-(3,4-Dichlorophenyl)-5-ethoxy-7-azatricyclo[5.3.0.0$^{4,8}$]decane, (1S,3S,4S,8R)-3-(4-chlorophenyl)-7-azatricyclo[5.3.0.0$^{4,8}$]decan-5-one, (1S,3S,4S,8R)-3-(4-chlorophenyl)-7-azatricyclo[5.3.0.0$^{4,8}$]decan-5-ol, (1S,3S,4S,8R)-3-(4-Chlorophenyl)-5-ethoxy-7-azatricyclo[5.3.0.0$^{4,8}$]decane, (1S,3S,4S,8R)-3-(3,4-Dichlorophenyl)-7-azatricyclo[5.3.0.0$^{4,8}$]decan-5-one O-benzyloxime, (1S,3S,4S,8R)-3-(3,4-Dichlorophenyl)-7-azatricyclo[5.3.0.0$^{4,8}$]decan-5-one oxime, (1S,3S,4S,8R)-3-(3,4-Dichlorophenyl)-7-azatricyclo[5.3.0.0$^{4,8}$]decan-5-one O-tert.-butyloxime, (1S,3S,4S,8R)-3-(3,4-Dichlorophenyl)-7-azatricyclo[5.3.0.0$^{4,8}$]decan-5-one O-ethyl-oxime, (1S,3S,4S,8R)-5-Allyloxy-3-(3,4-dichlorophenyl)-7-azatricyclo[5.3.0.0$^{4,8}$]decane, Ethyl (1S,3S,4S,8R)-2-[3-(3,4-dichlorophenyl)-7-azatricyclo[5.3.0.0$^{4,8}$]dec-5-yliden]acetate, (1S,3S,4S,8R)-3-(4-chlorophenyl)-7-azatricyclo[5.3.0.0$^{4,8}$]decan-5-one oxime, N1-[1S,3S,4S,8R)-3-(4-chlorophenyl)-7-azatricyclo[5.3.0.0$^{4,8}$]dec-5-yl acetamide, or (1S,3S,4S,8R)-3-(3,4-Dichlorophenyl)-7-azatricyclo[5.3.0.0$^{4,8}$]dec-5-yl amine or a pharmaceutically acceptable addition salt thereof.

4. A pharmaceutical composition, comprising an effective amount of a compound of claim 1 or 2, together with at least one pharmaceutically acceptable carrier or diluent.

5. A method for the preparation of a compound of the formula:

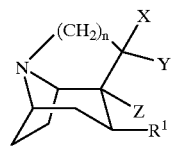
(I)

or any of its enantiomers or any mixture thereof, a pharmaceutically acceptable addition salt thereof or the N-oxide thereof wherein X and Y together form =O, =S, =NOR, =CR$^3$R$^4$, =N—CN, =N—NR$^7$R$^8$, —(CH$_2$)$_m$—, or —W'—(CH$_2$)$_p$—W"—, or one of X and Y is hydrogen and the other is —OR$^5$, —SR$^5$, or —NR$^5$R$^6$;

Z is hydrogen or —COOR$^9$;

R$^3$ and R$^4$ are independently hydrogen, halogen, alkyl, cycloalkyl, cycloalkylalkyl, alkenyl, alkynyl, alkoxy, phenyl, naphthyl, phenylalkyl, naphthylalkyl or —(CH$_2$)$_q$—COOR$^2$;

R$^2$, R$^5$ and R$^8$ are independently hydrogen, alkyl, cycloalkyl, cycloalkylalkyl, alkenyl, alkynyl, phenyl, naphthyl, or phenylalkyl, naphthylalkyl, —CO-alkyl, or —SO$_2$-alkyl;

R$^7$ and R$^8$ are independently hydrogen, alkyl, cycloalkyl, cycloalkylalkyl, alkenyl, alkynyl, phenyl, naphthyl, or phenylalkyl, naphthylalkyl;

R$^9$ is alkyl, alkenyl or alkynyl;

R$^1$ is alkyl, alkenyl, alkynyl, phenyl, naphthyl, or phenylalkyl, naphthylalkyl;

where said aryl groups may be substituted one or more times with substituents selected from the group consisting of halogen, $CF_3$, CN, alkoxy, cycloalkoxy, alkyl, cycloalkyl, alkenyl, alkynyl, $NH_2$, NH-alkyl, N—(alkyl)$_2$ and nitro;

W' and W" are each independently O or S;

n is 1, 2, 3, or 4;

m is 2, 3, 4, or 5;

p is 1, 2, 3, 4, or 5; and q is 0, 1, 2, 3, or 4;

comprising the steps of:
(a) performing ring-closure of a compound having the formula:

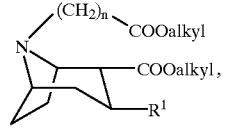
(II)

wherein n and R$^1$ are as defined above to form a compound of the formula:

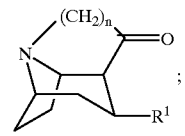
(III)

(b) thereafter converting said compound of the formula (III) to said compound of the formula (I) using conventional methods; and (c) thereafter optionally converting the compound obtained to another compound of the invention using conventional methods, and/or optionally forming a pharmaceutically acceptable salt thereof.

6. A method of treating a disorder or disease of a living animal body, including a human, which disorder or disease is responsive to the inhibition of monoamine neurotransmitter re-uptake, comprising the step of administering to such a living animal body, including a human, in need thereof a therapeutically effective amount of a compound according to claim 1.

7. A method of treating a disorder or disease of a living animal body, including a human, which disorder or disease is responsive to the inhibition of serotonin re-uptake, comprising the step of administering to such a living animal body, including a human, in need thereof a therapeutically effective amount of a compound according to claim 1.

8. The method of claim 6 or 7 wherein depression and related disorders selected from the group consisting of pseudodementia or Ganser's syndrome, obsessive compulsive disorders, panic disorders, memory deficits, attention deficit hyperactivity disorder, obesity, anxiety and eating disorders are treated.

* * * * *